(12) United States Patent
Carroll et al.

(10) Patent No.: US 6,320,934 B1
(45) Date of Patent: Nov. 20, 2001

(54) SENSOR CHARACTERIZATION IN MEMORY

(75) Inventors: Seamus Carroll, Cold Spring, NY (US); James Johnson, Ringwood, NJ (US)

(73) Assignee: AFP Imaging Corporation, Elmsford, NY (US)

( * ) Notice: Subject to any disclaimer, the term of this patent is extended or adjusted under 35 U.S.C. 154(b) by 0 days.

(21) Appl. No.: 09/812,008

(22) Filed: Mar. 19, 2001

Related U.S. Application Data

(63) Continuation-in-part of application No. 09/711,798, filed on Nov. 13, 2000, which is a continuation-in-part of application No. 09/603,395, filed on Jun. 26, 2000.

(51) Int. Cl.$^7$ ...................................................... H05G 1/64
(52) U.S. Cl. .......................................... 378/98.8; 378/98.7
(58) Field of Search ............................... 378/98.8, 98.12, 378/98.7, 97, 98

(56) References Cited

U.S. PATENT DOCUMENTS

| | | | |
|---|---|---|---|
| 5,182,624 | * | 1/1993 | Tran et al. ............................. 250/40 |
| 5,331,166 | * | 7/1994 | Yamamoto et al. ............ 250/370.11 |
| 5,744,806 | * | 4/1998 | Frojd ................................ 250/370.09 |
| 5,886,353 | * | 3/1999 | Spivey et al. .................... 250/370.09 |
| 5,912,942 | * | 6/1999 | Schick et al. ......................... 378/98.8 |
| 5,959,433 | * | 9/1999 | Rohde ................................... 320/108 |
| 6,069,935 | * | 5/2000 | Schick et al. ........................ 378/89.8 |
| 6,084,229 | * | 7/2000 | Pace et al. .......................... 250/208.1 |

* cited by examiner

Primary Examiner—Robert H. Kim
Assistant Examiner—Irakli Kiknadze
(74) Attorney, Agent, or Firm—Cooper & Dunham LLP

(57) ABSTRACT

An X-ray image sensor comprising an array of sensor elements and a sensor characterization storage device is provided. The sensor characterization storage device stores sensor characterization information identifying defects in the array of sensor elements. The X-ray image sensor may have an intergrated interpolator, and the interpolator processes image data from the array of sensor elements by using the sensor characterization information to correct for the defects in the array of sensor elements. An X-ray imaging system comprising the X-ray image sensor and a computer also is provided. The X-ray image sensor provides to the computer a signal corresponding to image data from the array of sensor elements. The X-ray image sensor provides to the computer the sensor characterization information, and the computer processes the image data using the sensor characterization information to correct for the defects in the array of sensor elements.

22 Claims, 8 Drawing Sheets

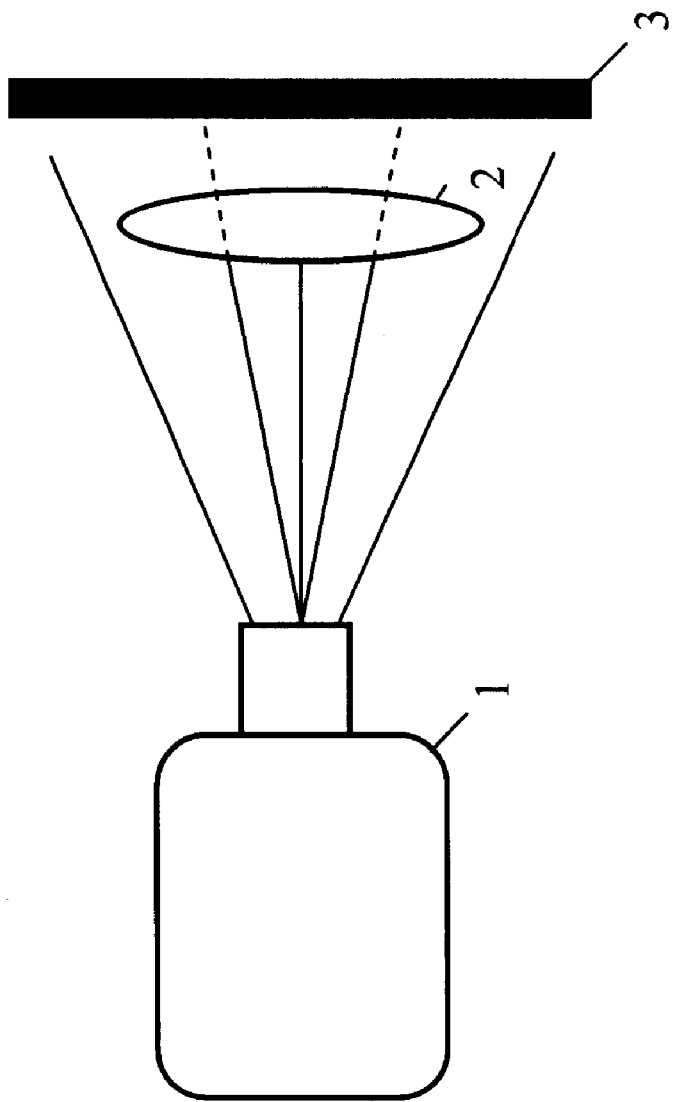

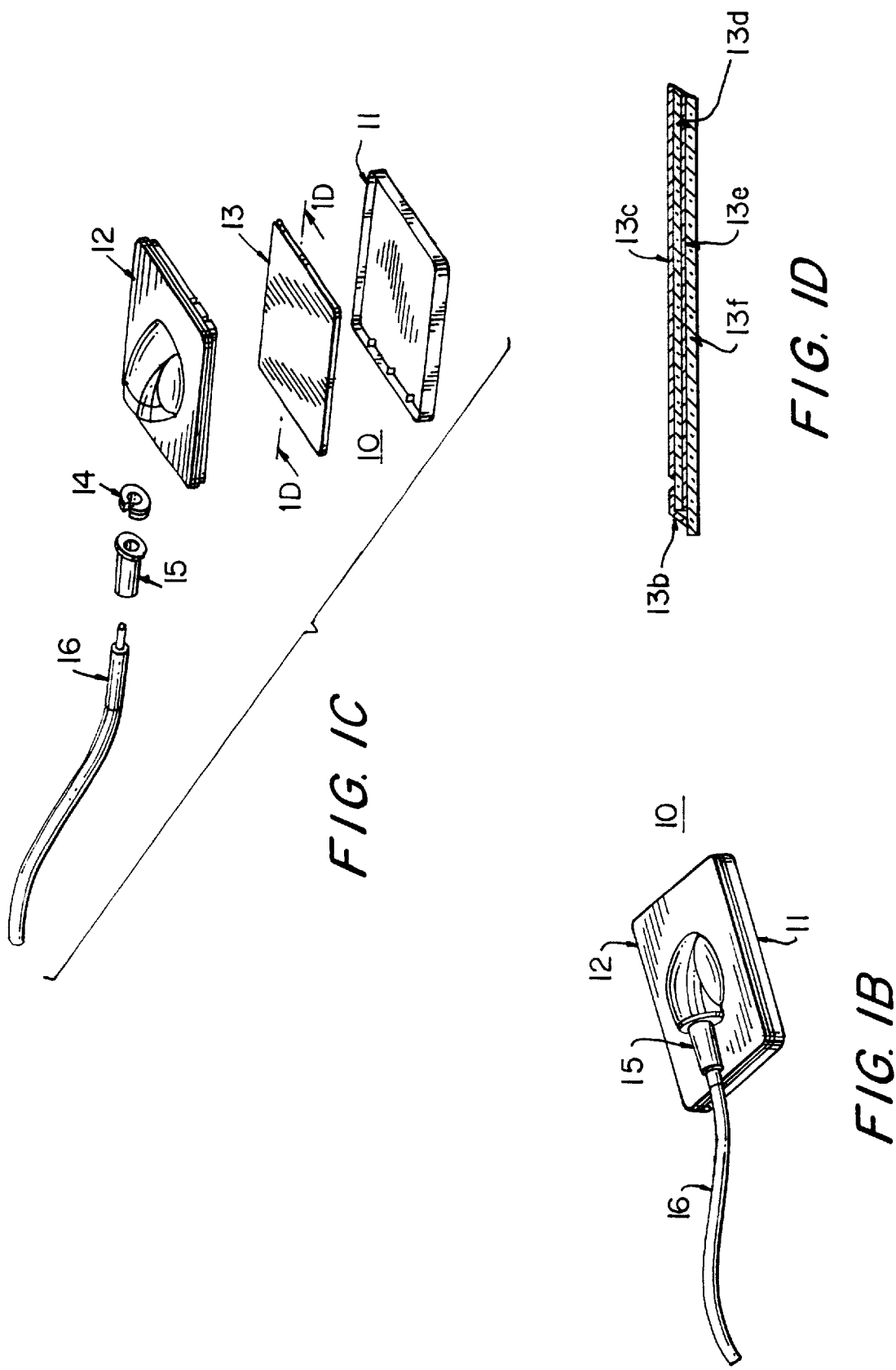

US 6,320,934 B1

SENSOR CHARACTERIZATION IN MEMORY

CROSS REFERENCE TO RELATED APPLICATIONS

This application is a continuation-in-part of U.S. patent application Ser. No. 09/711,798, filed Nov. 13, 2000 and entitled "DENTAL X-RAY IMAGING SYSTEM", which is a continuation-in-part of U.S. patent application Ser. No. 09/603,395, filed Jun. 26, 2000 and entitled "TRIGGERING OF SOLID STATE X-RAY IMAGERS WITH NON-DESTRUCTIVE READOUT CAPABILITY".

BACKGROUND OF THE INVENTION

The present invention relates to sensor characterization in an X-ray imaging system. In particular, the invention relates to storing sensor characterization in a memory resident in an X-ray image sensor.

X-ray image sensors comprising an array of active pixels are replacing film as the preferred tool for obtaining X-ray images of teeth and other body parts. An active pixel is a semiconductor device capable of converting an optical image into an electronic signal. When incident radiation interacts with a photosite, charge carriers are liberated and can be collected for sensing. The number of carriers collected in a photosite represents the amount of incident light impinging on the site in a given time period.

There are two basic devices, i.e., photodiodes and photogates, with many variants, employed to collect and sense charge carriers in a photosite. Variants of photodiodes include Pinned, P-I-N, Metal-Semiconductor, Heterojunction, and Avalanche. Photogate structures include Charge Coupled Devices (CCD), Charge Injection Devices (CID), and variants that include virtual phase, buried channel and other variations that utilize selective dopants which are used to control charge collection and transfer underneath and between the photogate(s) and the sense node.

Complementary metal-oxide semiconductor (CMOS) image sensors now also are available. Most CMOS imagers use Active Pixel Sensor (APS) technology, which utilizes an amplifier for each pixel. Due to process variations during the manufacture of these amplifiers, the actual gain and offset of each amplifier is slightly different from those of the other amplifiers. As a result, APS imagers suffer from high fixed pattern noise (FPN) problems. A solution to the variation in gain from one amplifier to another is to implement a unity gain amplifier (UGA) for every pixel. Each UGA requires the use of at least six field effect transistors (FETs).

An active column sensor (ACS) is described in U.S. Pat. No. 6,084,229. The ACS embodies the recognition that all but one of the FETs (the input FET) of each UGA for each pixel of a column in a CMOS active pixel sensor are redundant. In the ACS, the redundant FETs are absent, and replaced with a single shared UGA amplifier at each column for all the pixels in the column. The ACS has one dual input FET per pixel, and four or so shared FETs at each column.

Electronic image sensors, such as CCD or CMOS pixel sensors, have been adapted to be X-ray sensitive elements in dental and medical applications. The digital X-ray sensor is used to detect and record X-ray images which typically are downloaded to a personal computer via a cable. Examples of use of CCD-type and other X-ray image sensors in dental and/or medical environments are described in U.S. Pat. Nos. 5,671,738 and 5,744,806, which are incorporated herein by reference. An X-ray detector that comprises a plurality of CMOS active pixel sensors is described in U.S. Pat. Nos. 5,912,942 and 6,069,935.

Virtually all imaging sensors, CMOS, CCD, CID, etc., have defects, noise, etc., inherent in their design. One of the most common defects is dead pixels that do not record information. Other common defects include offset and variable sensitivity pixels, rows and columns. Typically, manufacturers of imaging sensors define an acceptable level of defects for their application, characterize these defects in production testing and create a software map (characterization) of the noise and defects of the sensor. This software map is then used in software filters to minimize the effect of the defects, so they do not appear in the images generated by the sensor. Without the filters, the dead pixels appear as black dots in the image.

In a typical X-ray imaging system in which image signals are supplied by an imaging sensor to a computer and processed by the computer before being displayed, a sensor characterization file corresponding to the sensor is stored on, for example, a floppy disk, and downloaded to such computer from the floppy disk. When the imaging sensor captures an image and supplies a corresponding image signal to the computer, the computer then applies a software filter using the sensor characterization file to eliminate the appearance of defects in the pixels and create an acceptable looking image which is displayed on a display or another medium. However, since users often forget the download step, images of poor quality frequently are obtained under those circumstances.

SUMMARY OF THE INVENTION

The present invention provides an X-ray image sensor comprising, in accordance with one embodiment, an array of sensor elements, and a sensor characterization storage device integrated with the X-ray image sensor. The sensor characterization storage device stores sensor characterization information identifying defects in the array of sensor elements. The sensor characterization information may include a list of sensor elements corresponding to dead pixels, or otherwise non-typical response pixels, rows or columns.

The present invention also provides an X-ray imaging system comprising, in accordance with one embodiment, an X-ray image sensor and a computer. The X-ray image sensor provides to the computer a signal corresponding to image data from the array of sensor elements.

The computer may retrieve the sensor characterization information from the X-ray image sensor and process the image data from the array of sensor elements using the sensor characterization information to correct for the defects in the array of sensor elements. The computer may replace data from a sensor element identified in the sensor characterization information as corresponding to a dead pixel, or other characterized defect, by interpolating data from sensor elements corresponding to live pixels surrounding the dead pixel.

The X-ray image sensor may have an integrated interpolator. The interpolator retrieves the sensor characterization information from the sensor characterization storage device, and processes image data read out from the array of sensor elements to correct for the defects in the array of sensor elements by using the sensor characterization information. The interpolator may replace data from a sensor element identified in the sensor characterization information as corresponding to a dead pixel, or other characterized defect, by interpolating data from sensor elements corresponding to live pixels surrounding the dead pixel or other characterized defect. The array of sensor elements may have a non-destructive readout structure. The interpolator may use the sensor characterization information to identify the sensor elements corresponding to live pixels surrounding the dead pixel, and read out the data from these sensor elements.

The X-ray image sensor may further comprise a processing section including a defect determination module. The defect determination module may determine at selected times the defects in the array of sensor elements by analyzing image data read out from the array of sensor elements. For example, the defect determination module in the processing section may, under command from the computer, perform the defect determination. In another embodiment, the computer generates the new sensor characterization information by analyzing the image data read out from the array of sensor elements to determine the defects in the array of sensor elements, and communicates the new sensor characterization information to a processing section in the X-ray image sensor.

The processing section uses the defects information provided by the defect determination module or the computer to generate new sensor characterization information and replace the sensor characterization information in the sensor characterization storage device with the new sensor characterization information. The information also, or alternatively, may be used to notify a user and/or a controlling device, and/or shut down the sensor.

BRIEF DESCRIPTION OF THE DRAWINGS

The above and numerous other objectives, features and advantages that may be achieved by the present invention would be more readily understood from the following detailed description by referring to the accompanying drawings wherein:

FIG. 1A shows a schematic view of an X-ray imaging system;

FIG. 1B shows a perspective view of a sensor capsule, according to one embodiment of the present invention;

FIG. 1C shows an exploded view of the sensor capsule assembly shown in FIG. 1B;

FIG. 1D shows a cross-sectional view taken along section line A—A of an X-ray sensor carrier shown in FIG. 1C;

DETAILED DESCRIPTION OF THE INVENTION

Figure 2A:
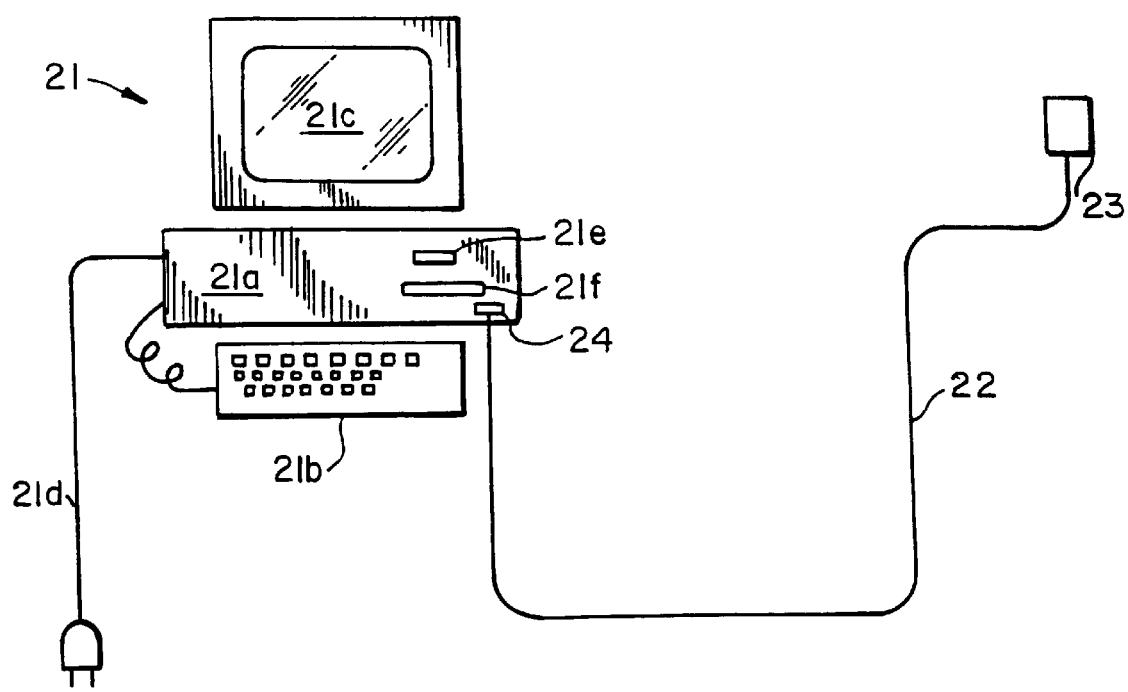
FIG. 2A shows a schematic view of a dental X-ray imaging system.

To further explain the invention, some embodiments are described in connection with the drawings and their supporting descriptions provided below.

FIG. 1A shows an X-ray imaging system with an X-ray generator 1 emitting X-rays, and arranged to irradiate an object 2 to be imaged. Part of the X-rays are absorbed by the object 2 to be imaged. An X-ray image sensor 3 is located behind that object. The X-ray photons which pass through the object are detected by the image sensor 3.

An X-ray image sensor, according to one embodiment of the present invention, will be described with reference to FIGS. 1B and 1C. Sensor capsule assembly 10 comprises capsule bottom 11, capsule top 12, sensor 13, bobbin 14, boot 15 and electrical cable 16. The X-ray detector 13 generates and transmits electrical signals through electrical cable 16 and an interface (described below) to an image processing/computing device. As discussed further below, peripheral processing may be performed by the computing device or by circuitry coupled to the computing device.

FIG. 1D is a magnified cross sectional view of an embodiment of the X-ray detector 13 of FIG. 1C, taken from section line A—A. In the embodiment shown in FIG. 1D, the X-ray detector includes a scintillator 13c on top of a semiconductor 13d, all supported on a passivated ceramic substrate 13f. In general terms, the scintillator 13c converts X-rays into visible light while the semiconductor 13d, in turn, converts the light into electrical signals representing the image.

The scintillator layer 13c is interposed between the X-ray source and the semiconductor layer 13d, to both protect the semiconductor from unwanted X-ray exposure and to provide conversion of the X-rays to visible light for direct detection by the semiconductor. X-ray-to-light converting materials that may be used for the scintillator include gadolinium oxysulphide, cesium iodide, cadmium tungstate, cadmium telluride, cadmium sulfide, calcium tungstate, zinc sulfide and zinc cadmium sulfide. Scintillating glass, such as for example terbium glass, or scintillating optical fibers also may be used. The scintillator 13c is positioned to be directly exposed to the X-rays which readily pass through a protective housing formed by capsule bottom 11 and capsule top 12.

The semiconductor 13d may be one of a number of semiconductor devices, including charge coupled devices (CCD), charge injection devices (CID), complementary metal oxide semiconductor (CMOS), etc., that have been used for imaging sensors which convert an optical image into an electronic signal. The semiconductor 13d preferably comprises an array of pixels and an integrated signal amplifier. The electrical signals produced by the semiconductor 13d are conveyed to the electrical cable 16 via conductive lead 13b. The conductive lead 13b also may convey electrical power and control signals from the computing device and/or interface (described below) to the semiconductor 13d.

The semiconductor 13d may sit on top of an X-ray absorption layer 13e. Absorption layer 13e absorbs any X-rays which are not converted by the scintillator 13c, to prevent those X-rays from hitting the patient, and absorbs any back-scattered radiation. X-ray absorbing materials that may be used for layer 13e include, for example, lead and tungsten.

The entire X-ray detector is enclosed in a protective enclosure formed by capsule bottom 11 and capsule top 12, which, along with bobbin 14 and boot 15, protects the X-ray detector from shock and moisture, while being permeable to X-ray radiation. Capsule bottom 11 and capsule top 12 may be made from, for example, aluminum or any one of many formulations of plastic known in the art.

X-ray imaging systems may be used in assorted digital X-ray imaging applications, including digital dental X-ray imaging to display and record dental radiographic images using a conventional dental X-ray source and an image processing/computing device. The digital X-ray imaging system may include hardware and software components.

Figure 2B:
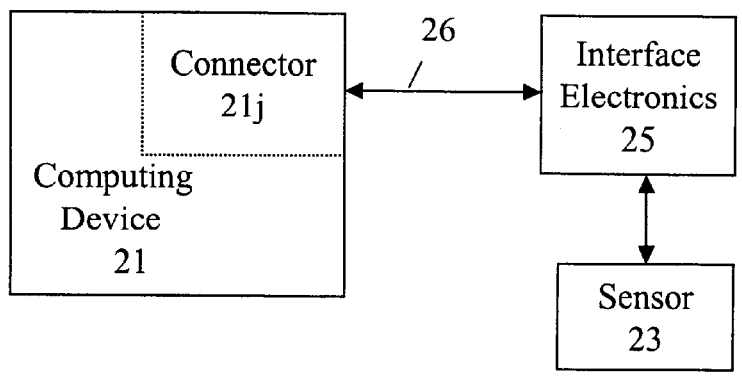
FIG. 2B shows a block diagram of a dental X-ray imaging system, according to an embodiment of the present invention.

FIGS. 2A and 2B show some of the hardware components that may be included in the system. The hardware components may include computer 21, image sensor 23, and interface electronics and an electrical cable 22 to link the sensor to the computer.

The interface electronics will be further described below. Interface electronics and connector 24, in the embodiment shown in FIG. 2A, are integrated with the packaging of computer 21. The user may disconnect the sensor from the computing device by unplugging a connector at the end of the electrical cable from the mating connector integrated with the computer, to switch to alternate sensor assemblies.

In another embodiment (FIG. 2B), there is an intermediate connection point 25 between sensor 23 and computing device 21. Interface electronics 25 is connected to computing device 21 via a standard-type, e.g., USB (Universal Serial Bus), electrical cable/connector 26. While the user could disconnect the sensor from the computing device by detaching the (e.g., USB) electrical cable/connector from a USB port 21$j$ of the computing device if desired, USB connectors, when the computing device is a personal or workstation computer, usually are provided on the back of the computer and therefore may be inconvenient to access. In addition, many low cost computing devices use low quality USB connectors which may fail in as little as one hundred (or even less) connection cycles. Thus, it is desirable to leave the USB cable connected to the computing device and have a high reliability interface 25 to connect the sensor to the computing device through electrical cable 26. Alternatively, cable 26 may be hard-wired to interface 25, and in such embodiments, the sensor may be disconnected from the computing device by disconnecting the connector at the end of cable 26 from the computing device.

Interface 25 may be, for example, a high reliability USB interface or a FireWire. Interface 25 may comprise a pair of mating connectors which may be detachable or permanently attached, as described below.

In another embodiment, the interface electronics and connector optionally may include a wireless interface for communicating with the image sensor through a wireless communication link. One of a number of wireless interfaces (e.g., Bluetooth), such as for an infrared optical link or radio frequency (e.g., spread spectrum RF) link, known in the art may be used. In such an embodiment, the X-ray image sensor also is provided with a wireless interface.

The wireless sensor may have, in one embodiment, a rechargeable battery for powering the sensor, which is placed in a recharger between uses. In another embodiment, the sensor has a capacitor which, instead of or along with a battery, stores the energy. When the sensor is removed from the charger and placed in the patient's mouth, the X-rays would trigger the sensor and discharge the capacitor, while one or more images would be held in memory on the sensor. Then, the sensor may be placed into a charger cradle, which may be integrated in the interface packaging. The charger cradle also may function as a data download (docking) station. When the image data is downloaded, the sensor is cleared and the charge storage device is recharged for the next use.

Other charge storage devices that are able to provide the power required by the sensor may be integrated with the wireless sensor. Each of the charge storage devices described above may be charged by the recharger through direct electrical connection or by inductive charging (see, e.g., U.S. Pat. No. 5,959,433).

Also, the interface package may be coupled to the computing device through a wireless (e.g., Bluetooth) interface rather than an electrical cable. Thus, connector 63$b$ of the interface base assembly 60, for example, may be replaced by such a wireless interface. The computing device, of course, would have a complementary wireless interface. Such an interface package may independently be powered by a battery or power supply.

Sensors of different sizes may be provided. In a dental application, a sensor that may be inserted into the patient's mouth preferably is provided. In one exemplary embodiment for a dental application, two sensors, having the approximate dimensions of 42 mm×30 mm×5 mm and 34 mm×25 mm×5 mm, respectively, are provided. Dimensions different from these exemplary dimensions may be selected, according to application and/or to accommodate an ergonomic or stylistic design. Image sensor 23 may be inserted into the patient's mouth and positioned to record the radiographic image of the teeth. The sensor may be connected to the computing device via electrical cable 22 with, for example, a standard USB computer interface in one embodiment.

Figure 2C:
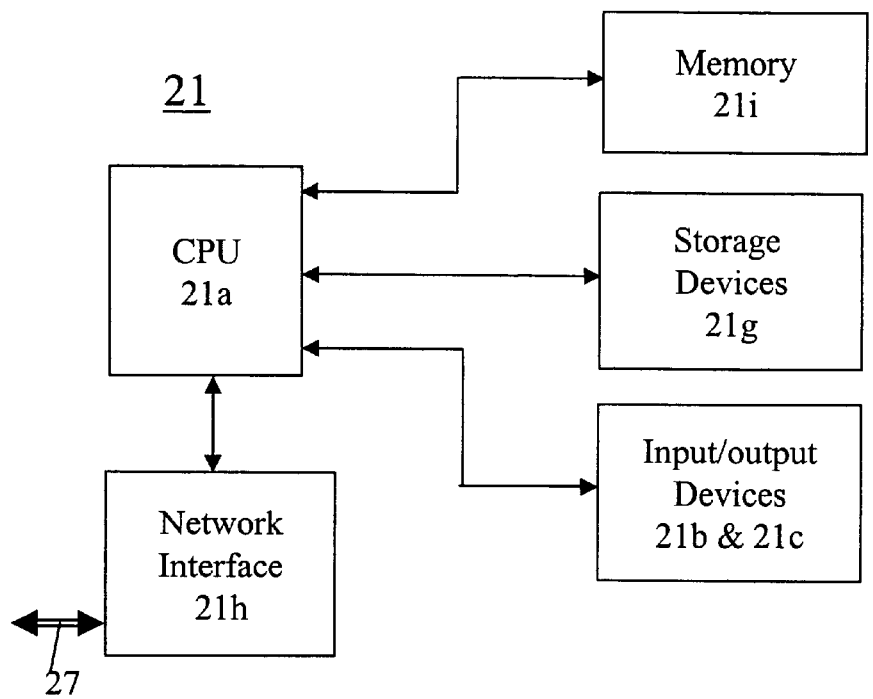
FIG. 2C shows a block diagram of a computing device which may be used in the dental X-ray imaging systems shown in FIGS. 2A and 2B.

Computer 21 typically is a personal computer (FIG. 2A) and may have the components shown in FIGS. 2A–2C. Computer 21, alternatively, may be, for example, a workstation computer, a notebook computer, or a handheld computing device, e.g., personal digital assistant. Computer 21 comprises CPU 21$a$, input devices 21$b$, output devices 21$c$, memory 21$i$ and one or more storage drives 21$g$, and may optionally also include power cord 21$d$ and network interface 21$h$. The storage drives may include, for example, floppy disk drive 21$e$, CD (or DVD) drive 21$f$ and a hard disk, etc.

The input/output devices may include a keyboard, mouse, microphone, track ball, stylus, monitor, printer/plotter, touch screen, speaker, etc., plus the appropriate device drivers and user interface software.

Network interface 21$h$ may be included for connecting to a network 27, which may be any one or a combination of the Internet, an intranet, an extranet, a LAN (local area network), a WAN (wide area network), a wireless network and other networks. Network interface 21$h$ includes the appropriate units for interfacing with the network 27, including, for example, Ethernet card, modem, wireless modem, etc.

Software components in the dental X-ray imaging system may include a graphical user interface to control the hardware, image management functions and interfaces to other dental software packages. The software components also include assorted device drivers, including a wireless communication driver if a wireless interface is provided.

The software components may be stored on a floppy disk, CD or another storage medium, and installed on the computing device. The software components alternatively (or also) may be communicated through the network interface via a network, such as the Internet, and/or a wireless transmission medium. Further, each software component may comprise one or more segments, subsets of which are retrieved, from the computer hard disk or via the network or transmission medium, as need arises.

The functions of the system may depend on the hardware and software implementation. The functions may be combined/split or otherwise modified to ease the design, manufacture and serviceability of the system. Thus, image capture control functions may be implemented by, for example, a combination of software and hardware components. The following exemplary image capture functions may be provided: initialize the system, i.e. communicate with the sensor over the USB (or wireless means) and wake it up if required; obtain system status; prepare for exposure by commanding the hardware to enter a wait-for-exposure mode and erase image currently stored in system memory; detect capture of an image, and signal client software that an image has been captured and is ready for upload; initialize image data transfer, and send command to start upload of image data to the system (the image data may be sent as a complete image or streamed as available); a command is sent from client to the system to exit wait-for-exposure mode and enter standby mode; and retrieve integration time.

Figure 3:
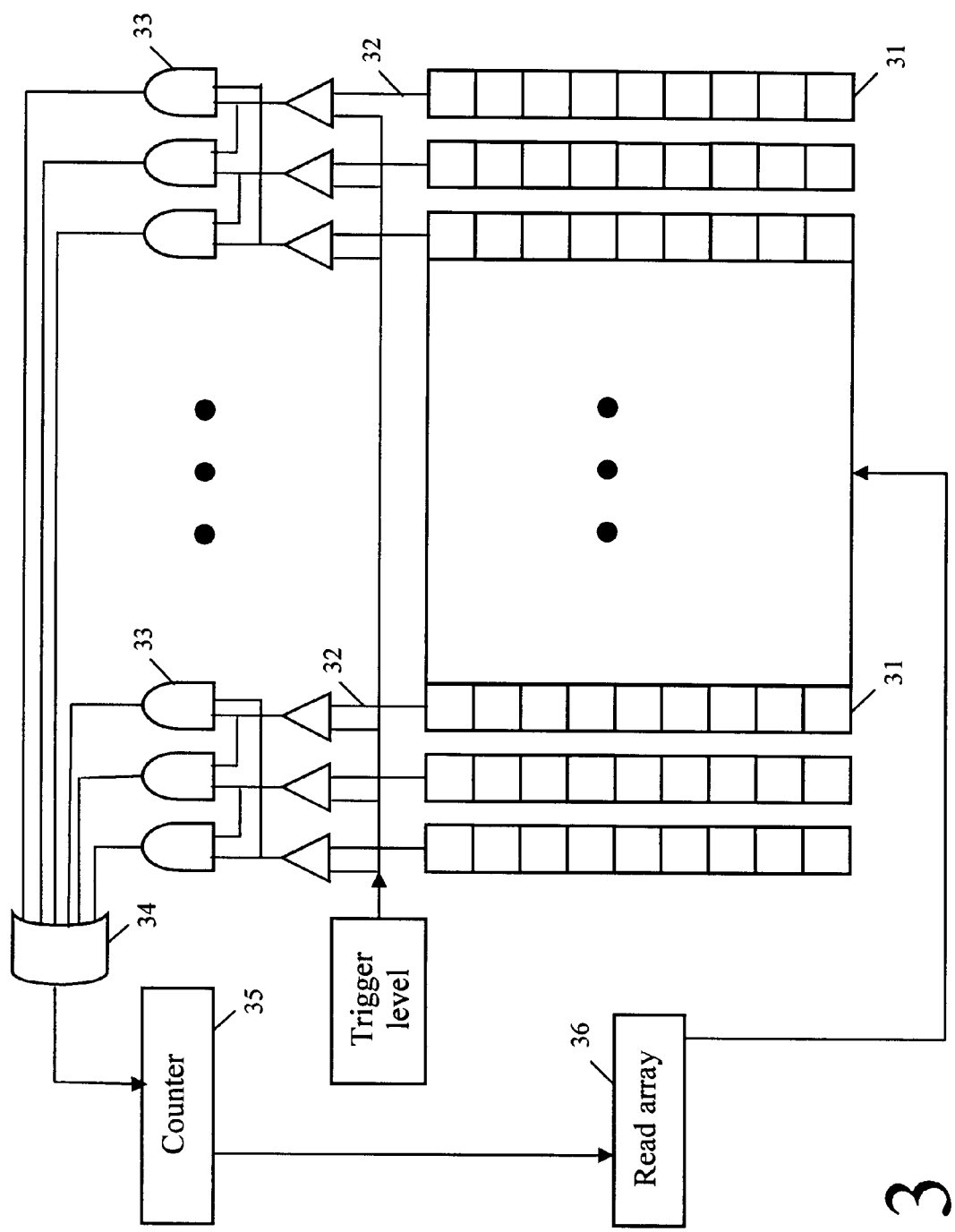
FIG. 3 shows a schematic view of some circuitry in an X-ray image sensor, according to one embodiment of the present invention.

FIG. 3 shows image capture circuitry in X-ray image sensor 30. The X-ray image sensor has a plurality of columns 31 of pixels, although only two sets of columns selected as reference pixels are shown in FIG. 3. The image capture circuitry also includes Boolean logic units 33 and 34, counter 35 and timing/control block 36, which includes row and column addressing circuits for readout of the pixels.

To synchronize the image capture sequence of the image sensor with the output of an X-ray source, in accordance with one embodiment, the sets of columns of reference pixels are selected. X-ray image sensor 30 has preferably random, non-destructive readout. Until exposure is detected, the selected sets of columns are read out and, for each of the selected columns, charge from the reference pixels in the column is averaged together for one low noise signal 32 per column. The columns in each set are logically compared to determine whether at least two out of three columns of summed charges in each set exceeds a predetermined threshold level. Boolean logic units 33 and 34 are used to verify that two out of three columns have exceeded the predetermined threshold level. Either set of three columns may trigger a counter 35 that then would count down a minimum of, for example, 800 milliseconds before causing one frame of video to be read out by block 36. The selected columns of pixels are reset at, for example, a 10 Hz frame rate to eliminate any possibility of dark current build up while waiting for an X-ray event.

Additional image capture features and imager trigger features are described in U.S. patent applications Ser. Nos. 09/711,798, filed Nov. 13, 2000, and 09/603,395, filed Jun. 26, 2000, which are incorporated herein by reference.

Figure 4:
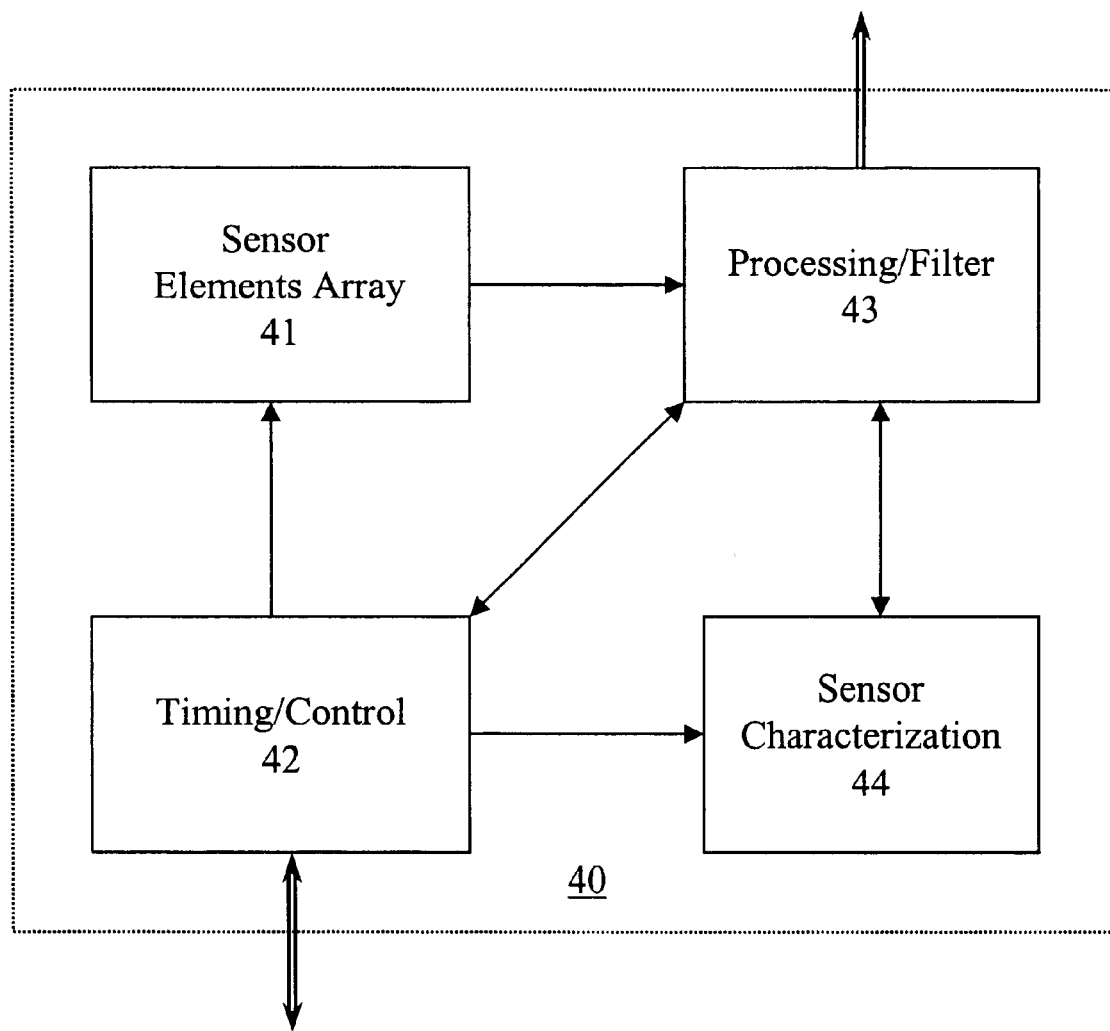
FIG. 4 shows a block diagram of some components of an X-ray imaging sensor, according to one embodiment of the present invention.
Figure 5:
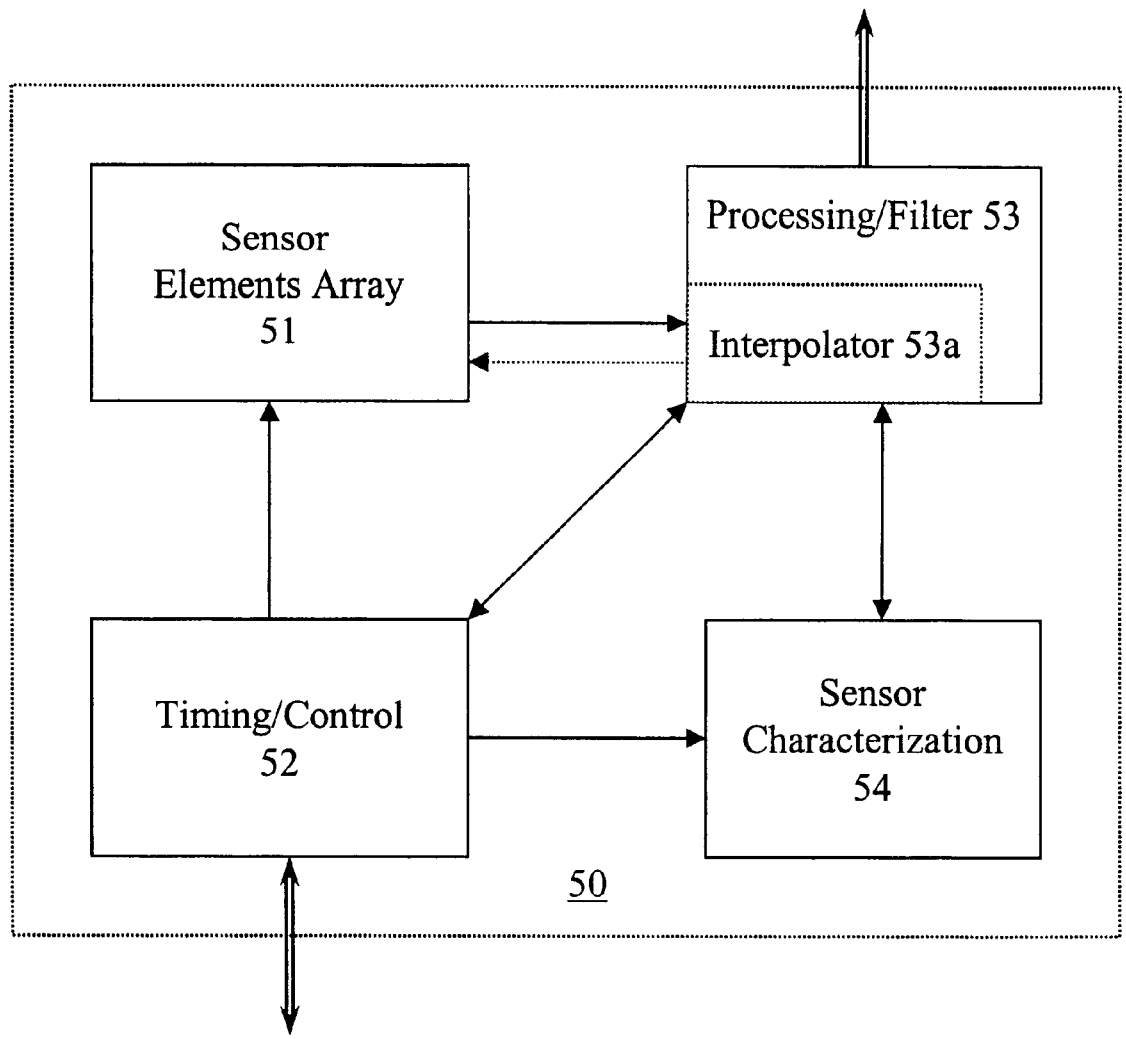
FIG. 5 shows a block diagram of some components of an X-ray imaging sensor, according to another embodiment of the present invention.
Figure 6:
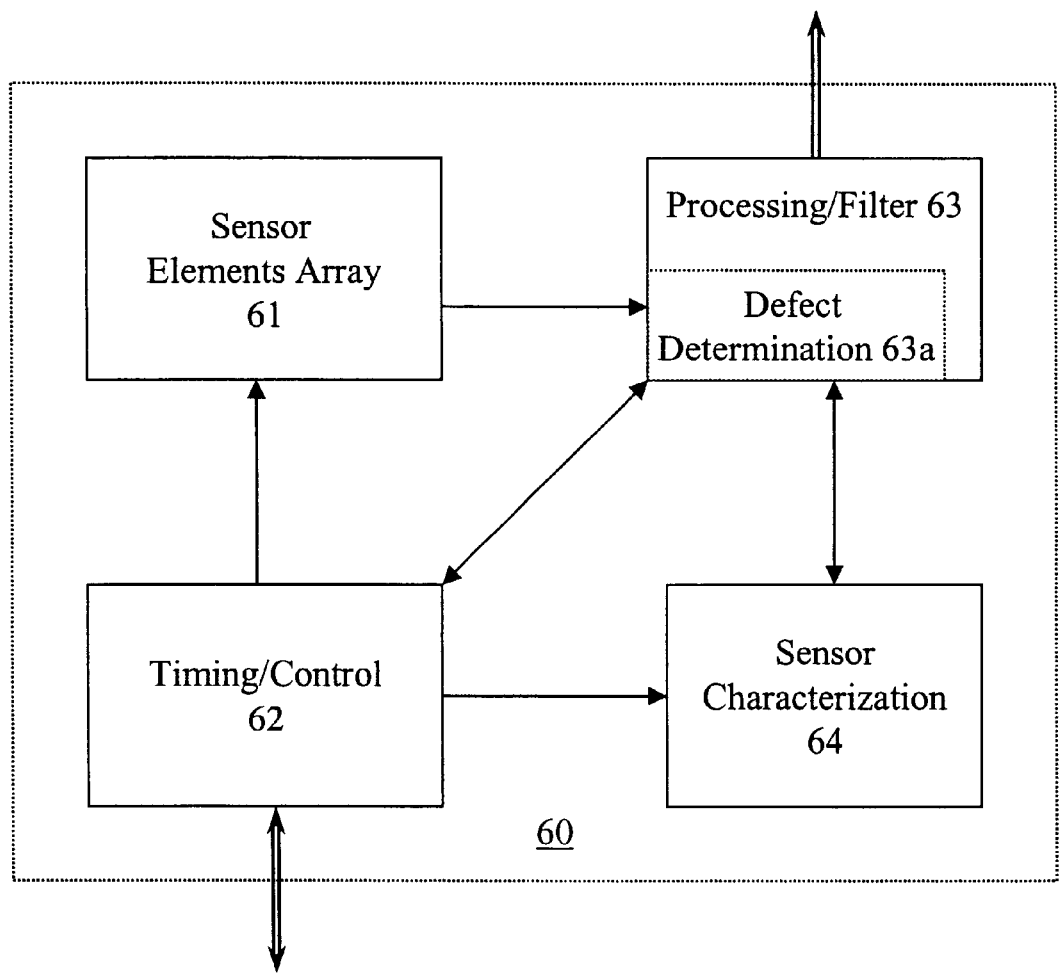
FIG. 6 shows a block diagram of some components of an X-ray imaging sensor, according to yet another embodiment of the present invention.

Storage and use of sensor characterization information further will be described below, with reference to FIGS. 4–6.

In accordance with one embodiment, an X-ray image sensor 40 comprising an array of sensor elements 41, and an integrated sensor characterization storage device 44 is provided. The X-ray image sensor is typically used in an X-ray imaging system which also comprises a computing device. The X-ray image sensor may provide (through an optional interface) to the computing device a signal corresponding to image data from the array of sensor elements.

The sensor characterization storage device 44 stores sensor characterization information identifying defects in the array of sensor elements. The sensor characterization information may include a list of sensor elements corresponding to dead or otherwise defective pixels, rows, columns or regions. The sensor characterization information may also include information that describe other "defects" in the sensor elements which require corrections/adjustments in the processing. For example, some sensors have high fixed pattern noise problems, which may be identified by the sensor characterization information.

The sensor characterization storage device may be one or a combination of buffers, registers and memories [e.g., read-only memory (ROM), programmable ROM (PROM), erasable PROM (EPROM), electrically erasable PROM (EEPROM), non-volatile random access memory (NOVRAM)]. In any event, the sensor characterization storage device is preferably non-volatile so that the sensor characterization information is not lost when the regular power source of the sensor is removed. The sensor characterization storage device preferably is also programmable so that the sensor characterization information may be replaced by new sensor characterization information, without replacing the physical device.

The X-ray image sensor 40 also has a timing/control section 42 which drives operation of the array of sensor elements. The control circuits includes row and column addressing circuits, and optionally can command readout of any area of interest within the array. The area of interest may be specified by command from the computing device. The timing and control circuit controls the phase in the address sequences for accessing the rows and columns. Portions of the sensor and system which are well known in the art, such as the circuitry for reading out a selected area of interest, will not be described herein in detail.

Timing/control section 42 may also provide a programmable integration time, specified by, for example, the external computing device. The sensor is provided with inputs for receiving, in addition to a power supply in one embodiment, commands and data, such as defining integration time and windowing parameters, from the computing device.

Timing/control section 42 may also provide control over a processing/filter section 43 of the X-ray image sensor. The processing/filtering section 43 processes image data from the sensor elements to output a signal corresponding to the image data to the computing device. The processing may include, for example, converting analog output from the sensor array to digital stream (of bits). Alternatively, the analog-to-digital conversion circuitry may be included in the sensor array. The processing also may include converting the serial stream of bits to parallel lines. Alternatively, the serial-to-parallel conversion is performed external to the sensor, such as by the interface or by the computing device.

In one embodiment, the processing section 43 under command of the computing device through the control section 42 retrieves the sensor characterization information from the sensor characterization storage device 44 and forwards the sensor characterization information to the computing device. The computing device processes the image data from the array of sensor elements 41 using the sensor characterization information to correct for the defects in the array of sensor elements. For example, the computing device may replace data from a sensor element identified in the sensor characterization information as corresponding to a dead pixel by interpolating data from sensor elements corresponding to live pixels surrounding the dead pixel to calculate a value for the dead pixel.

In another embodiment (FIG. 5), processing section 53 includes an interpolator 53a. The interpolator 53a retrieves the sensor characterization information from the sensor characterization storage device, receives image data read out from the array of sensor elements, and processes the image data using the sensor characterization information to correct for the defects in the array of sensor elements. The interpolator may use the sensor characterization information corresponding to a dead pixel, in one embodiment, to identify the sensor elements corresponding to live pixels surrounding the dead pixel, and read out the data from these selected live sensor elements. Under such circumstances, the array of sensor elements should have non-destructive readout. In any event, the interpolator replaces data from the sensor element corresponding to the dead pixel by, for example, interpolating the data from the surrounding live pixels.

The computing device may generate new sensor characterization information by analyzing the image data read out from the array of sensor elements provided by the sensor to determine defects in the array of sensor elements. The computing device then communicates the new sensor characterization information to the processing section in the X-ray image sensor.

In another embodiment (FIG. 6), processing section 63 in X-ray image sensor 60 includes a defect determination module 63a. The defect determination module 63a, at selected times, determines the defects in the array of sensor elements by analyzing image data read out from the array of sensor elements. In one embodiment, the defect determination module may include for example, a frame memory (or other, preferably non-volatile, storage device), which stores, for each sensor element, a corresponding pixel value of the sensor element in a preceding frame. The defect determination module may compare the value read out from a subject sensor element of the array with a corresponding value of the sensor element in a previous frame which is stored in the frame memory. If the rate of change between the two values is below a minimum rate, the sensor element may be marked as a dead or defective pixel candidate.

In one embodiment, the defect determination is performed by the defect determination module during a sensor test mode in which the sensor is exposed to the X-ray source with no intervening objects therebetween for a predetermined time duration. In another embodiment, the defect determination module, under command from the computing device, uses the image data read out from the array of sensor elements, during normal operation, to determine the defects in the array of sensor elements.

In any event, the processing section uses the defects information determined by the defect determination module or by the computing device to generate new sensor characterization information and replace the sensor characterization information in the sensor characterization storage device with the new sensor characterization information.

In an X-ray imaging system according to an embodiment of the present invention, the sensor characterization is stored in the sensor electronics. This allows the user to plug the X-ray image sensor into any computer without the need to load the sensor characterization onto the computer from a floppy disk. With the sensor characterization stored in the electronics in the sensor assembly, the download from the floppy disk is eliminated, thereby removing risk of user error and poor image quality. Since the sensor characterization stays with the sensor, the plug-and-play sensor is much more user friendly and prevents many service calls when the user forgets to load the characterization onto a computer and/or forgets the floppy disk.

While embodiments of the present invention have been described in detail above, it should be understood that the invention is not limited to the precise embodiments described.

For example, in the embodiments described above, the sensor array preferably has non-destructive readout. Non-destructive readout, however, is not required. When the sensor array does not have non-destructive readout, an additional storage device, for example, may be provided. The additional storage device serves as a frame buffer/memory for storing data sequentially read out from the array. Thereafter, the data is retrieved from the storage device and processed, for example, before being output to the computing device or returned to the frame buffer. Thus, for example, the interpolator would retrieve data corresponding to live pixels surrounding a subject dead pixel from the frame buffer, and then store the interpolated value in an address of the frame buffer corresponding to the dead pixel.

As another example, the sensor characterization storage device along with the processing section may be programmable circuits [e.g., programmable array logic (PAL), programmable logic array (PLA), other programmable circuits, etc.] rather than storage device. Thus, the sensor characterization information may be, for example logic embodied in the programmable circuits, which process image data from the sensor array while decoding row and column addresses supplied from the control section to the sensor array.

The sensor characterization storage device, as well as the processing section and timing/control, may be integrated with the sensor semiconductor on a single IC (integrated circuit) chip, particularly when CMOS technology is used. Alternatively, the sensor may comprise two or more discrete devices integrated devices within the sensor packaging. Thus, the sensor characterization storage device may be, for example, a memory chip residing on a printed circuit board that also hosts a sensor chip.

Further, while the description herein (including in the appended claims) sometimes refers to pixels alone, such pixels, as one skilled in the art would understand and appreciate, may include rows, columns and regions.

Other improvements and modifications which become apparent to persons of ordinary skill in the art after reading this disclosure, the drawings and the appended claims are deemed within the spirit and scope of the present invention.

What is claimed is:

1. An X-ray image sensor comprising:
an array of sensor elements; and
a sensor characterization storage device integrated in the X-ray image sensor,
wherein the sensor characterization storage device stores sensor characterization information identifying defects in the array of sensor elements.

2. The X-ray image sensor of claim 1, wherein the sensor characterization information includes a list of sensor elements corresponding to dead pixels or otherwise non-typical response pixels, rows or columns.

3. The X-ray image sensor of claim 1 further comprising an interpolator, wherein the interpolator retrieves the sensor characterization information from the sensor characterization storage device, receives a signal corresponding to image data read out from the array of sensor elements, and processes the image data using the sensor characterization information to correct for the defects in the array of sensor elements.

4. The X-ray image sensor of claim 3, wherein the interpolator replaces data from a sensor element identified in the sensor characterization information as corresponding to a dead pixel by interpolating data from sensor elements corresponding to live pixels surrounding the dead pixel.

5. The X-ray image sensor of claim 4, wherein the array of sensor elements have non-destructive readout.

6. The X-ray image sensor of claim 5, wherein the interpolator uses the sensor characterization information to identify the sensor elements corresponding to live pixels surrounding the dead pixel, and reads out the data from said sensor elements.

7. The X-ray image sensor of claim 1 further comprising a processing section having a defect determination module, wherein the defect determination module periodically determines the defects in the array of sensor elements by analyzing image data read out from the array of sensor elements, and the processing section, based on the defects information determined by the defect determination module, performs at least one of the following: (a) generates new sensor characterization information and replace the sensor characterization information in the sensor characterization storage device with the new sensor characterization information; (b) notifies at least one of a user and a controlling device; and (c) shuts down the sensor.

8. The X-ray image sensor of claim 1, wherein the X-ray image sensor provides to a computing device the sensor characterization information and provides to the computing device a signal corresponding to image data read out from the array of sensor elements, and the computing device processes the image data using the sensor characterization information to correct for the defects in the array of sensor elements.

9. The X-ray image sensor of claim 8, wherein the computing device replaces data from a sensor element identified in the sensor characterization information as corresponding to a dead pixel by interpolating data from sensor elements corresponding to live pixels surrounding the dead pixel.

10. The X-ray image sensor of claim 9 further comprising a processing section having a defect determination module, wherein the defect determination module under command from the computing device uses the image data read out from the array of sensor elements to determine the defects in the array of sensor elements, and the processing section uses the defects information determined by the defect determination module to generate new sensor characterization information and replaces the sensor characterization information in the sensor characterization storage device with the new sensor characterization information.

11. The X-ray image sensor of claim 1, wherein the sensor including the sensor characterization storage device is integrated in an IC chip.

12. An X-ray imaging system comprising:
an X-ray image sensor having an integrated sensor characterization storage device, wherein the sensor characterization storage device stores sensor characterization information identifying defects in an array of sensor elements in the X-ray image sensor; and
a computer,
wherein the X-ray image sensor provides to the computer a signal corresponding to image data from the array of sensor elements.

13. The X-ray imaging system of claim 12, wherein the sensor characterization information includes a list of sensor elements corresponding to dead pixels.

14. The X-ray imaging system of claim 12, wherein the computer retrieves the sensor characterization information from the X-ray image sensor, and processes the image data from the array of sensor elements using the sensor characterization information to correct for the defects in the array of sensor elements.

15. The X-ray imaging system of claim 14, wherein the computer replaces data from a sensor element identified in the sensor characterization information as corresponding to a dead pixel by interpolating data from sensor elements corresponding to live pixels surrounding the dead pixel.

16. The X-ray imaging system of claim 12, wherein
the X-ray image sensor further comprises a processing section,
the computer generates new sensor characterization information by analyzing the image data read out from the array of sensor elements to determine the defects in the array of sensor elements, and communicates the new sensor characterization information to the processing section in the X-ray image sensor, and
the processing section replaces the sensor characterization information in the sensor characterization storage device with the new sensor characterization information from the computer.

17. The X-ray imaging system of claim 12, wherein
the X-ray image sensor further comprises a processing section having a defect determination module,
the defect determination module under command from the computer uses the image data read out from the array of sensor elements to determine the defects in the array of sensor elements, and
the processing section uses the defects information determined by the defect determination module to generate new sensor characterization information and replaces the sensor characterization information in the sensor characterization storage device with the new sensor characterization information.

18. The X-ray imaging system of claim 12, wherein an interpolator in the X-ray image sensor retrieves the sensor characterization information from the sensor characterization storage device, and processes the image data read out from the array of sensor elements using the sensor characterization information to correct for the defects in the array of sensor elements to provide a signal corresponding to adjusted image data.

19. The X-ray imaging system of claim 18, wherein the interpolator replaces data from a sensor element identified in the sensor characterization information as corresponding to a dead pixel by interpolating data from sensor elements corresponding to live pixels surrounding the dead pixel.

20. The X-ray imaging system of claim 19, wherein the array of sensor elements have non-destructive readout.

21. The X-ray imaging system of claim 20, wherein the interpolator uses the sensor characterization information to identify the sensor elements corresponding to live pixels surrounding the dead pixel, and reads out the data from said sensor elements.

22. The X-ray imaging system of claim 12, wherein the X-ray image sensor including the integrated sensor characterization storage device is integrated in an IC chip.

* * * * *